United States Patent
Stewart et al.

(10) Patent No.: US 12,239,461 B2
(45) Date of Patent: Mar. 4, 2025

(54) HEARING ASSISTANCE DEVICE HOUSING FOR IMPROVED BIOMETRIC SENSING

(71) Applicant: Starkey Laboratories, Inc., Eden Prairie, MN (US)

(72) Inventors: Jay Stewart, Eden Prairie, MN (US); Michael Karl Sacha, Chanhassen, MN (US); Kyle Olson, St. Louis Park, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 424 days.

(21) Appl. No.: 17/597,870

(22) PCT Filed: Jul. 30, 2020

(86) PCT No.: PCT/US2020/044296
§ 371 (c)(1),
(2) Date: Jan. 27, 2022

(87) PCT Pub. No.: WO2021/022063
PCT Pub. Date: Feb. 4, 2021

(65) Prior Publication Data
US 2022/0257186 A1     Aug. 18, 2022

Related U.S. Application Data

(60) Provisional application No. 62/880,987, filed on Jul. 31, 2019.

(51) Int. Cl.
*H04R 25/00*     (2006.01)
*A61B 5/00*      (2006.01)
(Continued)

(52) U.S. Cl.
CPC .............. *A61B 5/6815* (2013.01); *A61B 5/02* (2013.01); *A61B 5/14551* (2013.01); *A61B 5/24* (2021.01);
(Continued)

(58) Field of Classification Search
CPC . H04R 2225/77; H04R 25/652; H04R 25/658
(Continued)

(56) References Cited

U.S. PATENT DOCUMENTS

2012/0209101 A1\*  8/2012  Kidmose .............. H04R 25/652
                                                         29/874
2016/0310028 A1   10/2016  Kidmose et al.
(Continued)

FOREIGN PATENT DOCUMENTS

WO    WO-2021022063 A1    2/2021

OTHER PUBLICATIONS

"International Application Serial No. PCT US2020 044296, International Preliminary Report on Patentability mailed Feb. 10, 2022", 8 pgs.

(Continued)

*Primary Examiner* — Phylesha Dabney
(74) *Attorney, Agent, or Firm* — Schwegman Lundberg & Woessner, P.A.

(57) ABSTRACT

Disclosed herein, among other things, are apparatus and methods for a hearing assistance device housing for biometric sensing. In various embodiments, a hearing assistance device for a wearer includes a housing customized to conform to a continuous section of an inner portion of an ear of the wearer and to extend radially to one or more edges of a conchal bowl of the ear. The housing is configured to be placed in the inner portion of the ear of the wearer, and a biometric sensor is included on a surface of the housing. According to various embodiments, the housing is config- (Continued)

ured to maintain contact of the biometric sensor with the inner portion of the ear of the wearer during activity of the wearer, to enhance accuracy of biometric sensing.

20 Claims, 6 Drawing Sheets

(51) Int. Cl.
    *A61B 5/02*     (2006.01)
    *A61B 5/1455*     (2006.01)
    *A61B 5/24*     (2021.01)

(52) U.S. Cl.
    CPC ......... *A61B 5/6843* (2013.01); *H04R 25/652* (2013.01); *H04R 25/658* (2013.01); *H04R 2225/77* (2013.01)

(58) Field of Classification Search
    USPC .......................................................... 381/328
    See application file for complete search history.

(56) References Cited

U.S. PATENT DOCUMENTS

| | | |
|---|---|---|
| 2019/0046794 A1 | 2/2019 | Goodall et al. |
| 2019/0116415 A1 | 4/2019 | Qian et al. |
| 2019/0133469 A1 | 5/2019 | Just et al. |

OTHER PUBLICATIONS

"European Application Serial No. 20757157.1, Communication pursuant to Article 94(3) EPC, mailed Nov. 10, 2023", 10 pgs.
"International Application Serial No. PCT/US2020/044296, International Search Report mailed Sep. 21, 2020", 4 pgs.
"International Application Serial No. PCT/US2020/044296, Written Opinion mailed Sep. 21, 2020", 6 pgs.

* cited by examiner

HEARING ASSISTANCE DEVICE HOUSING FOR IMPROVED BIOMETRIC SENSING

CLAIM OF PRIORITY

This patent application is a U.S. National Stage Filing under 35 U.S.C. 371 from International Application No. PCT/US2020/044296, filed on Jul. 30, 2020, which claims the benefit of priority to U.S. Provisional Application Ser. No. 62/880,987, filed Jul. 31, 2019, each of which are incorporated by reference herein in their entirety.

TECHNICAL FIELD

This document relates generally to hearing assistance systems and more particularly to a hearing assistance device housing for improved biometric sensing.

BACKGROUND

Examples of hearing assistance devices, also referred to herein as hearing devices or hearing instruments, include both prescriptive devices and non-prescriptive devices. Specific examples of hearing assistance devices include, but are not limited to, hearing aids, headphones, assisted listening devices, and earbuds.

Hearing aids are used to assist patients suffering hearing loss by transmitting amplified sounds to ear canals. In one example, a hearing aid is worn in and/or around a patient's ear. Hearing aids may include processors and electronics that improve the listening experience for a specific wearer or in a specific acoustic environment.

In addition, biometric sensors may be included in or on a hearing instrument to collect physiological data from the wearer. However, biometric sensing in the ear using a skin-contact sensor can be challenging due to variable geometry of the ear and relative movement of the ear during activity of the wearer.

There is a need in the art for an improved hearing assistance device housing, or shell, for biometric sensing.

SUMMARY

Disclosed herein, among other things, are apparatus and methods for a hearing assistance device housing for biometric sensing. In various embodiments, a hearing assistance device for a wearer includes a housing customized to conform to a continuous section of an inner portion of an ear of the wearer and to extend radially to one or more edges of a conchal bowl of the ear. The housing is configured to be placed in the inner portion of the ear of the wearer, and a biometric sensor is included on a surface of the housing. According to various embodiments, the housing is configured to maintain contact of the biometric sensor with the inner portion of the ear of the wearer during activity of the wearer, to enhance accuracy of biometric sensing. Some embodiments include a gap or void in the housing, such that the housing forms a loop structure.

Various aspects of the present subject matter include a housing for a hearing assistance device. In various embodiments, the housing includes a surface configured to conform to a continuous section of an inner portion of an ear of the wearer and to extend radially to one or more edges of a conchal bowl of the ear. The housing further includes a biometric sensor on the surface, and the housing is configured to maintain contact of the biometric sensor with the inner portion of the ear of the wearer during activity of the wearer, to enhance accuracy of biometric sensing, in various embodiments. Some embodiments include a gap or void in the housing, such that the housing forms a loop structure.

Various aspects of the present subject matter include a method of forming a hearing assistance device for a wearer. The method includes providing a housing customized to conform to a continuous section of an inner portion of an ear of the wearer and to extend radially to one or more edges of a conchal bowl of the ear, the housing configured to be placed in the inner portion of the ear of the wearer. The method further includes providing a biometric sensor on a surface of the housing, according to various embodiments. The method also includes configuring the housing to maintain contact of the biometric sensor with the inner portion of the ear of the wearer during activity of the wearer, to enhance accuracy of biometric sensing, in various embodiments. The housing is constructed of a material that is compliant to maintain contact with the inner portion of the ear of the wearer when the inner portion moves due to the activity, according to various embodiments.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1A:
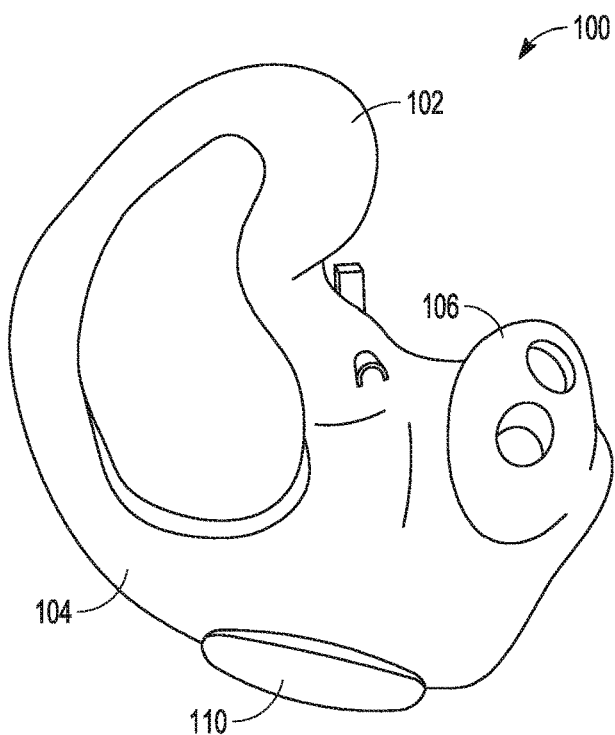
FIGS. 1A-1B illustrate a hearing assistance device housing for improved biometric sensing, according to various embodiments of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present detailed description will discuss hearing assistance devices using the example of hearing aids. Other hearing assistance devices include, but are not limited to, those in this document. It is understood that their use in the description is intended to demonstrate the present subject matter, but not in a limited or exclusive or exhaustive sense.

When using a hearing assistance device shell to perform biometric sensing, such as heart rate monitoring, it can be difficult to achieve high accuracy due to varying ear geometry of wearers as well as relative movement of the ear during activity of the wearers. When the ear geometry of a wearer is known, a custom shell can be made to exactly fit in the ear canal. For aesthetic reasons the amount of the shell outside of the ear canal should be minimized. However, by minimizing the shell volume external to the ear canal, the shell loses many of the contact points to keep the sensor from moving during activity of the wearer (e.g. walking, jogging, exercise, chewing, talking, etc.). Currently, a standard ear piece configuration is used which provides less accurate signal quality.

Providing a solid skin interface for the sensors provides noise suppression in many biometric signals and makes it possible to measure these signal continuously across many different activities. The present subject matter provides for using a skeleton shell with a hearing assistance device, to which sensors can be added in the ear as the interface to the body is consistent which provides the highest accuracy biometric signals.

To improve sensor contact to the skin, the housing should contact the wearer's inner ear in at least three places, creating a force triangle to stabilize the sensor during movement. This would be aesthetically unfavorable as the shell would be greater than or equal to half the size of the concha area in the ear. However, the "skeleton" housing of the present subject matter can be used to provide a continuous contact with the ear in more than three locations to maximize the stability of the sensor within the ear. This stable platform allows not just heart rate measurement, but any type of sensor that require the relative motion between the sensor and the skin to be minimized.

In various embodiments, biometric sensors that benefit from a stable ear shell with robust skin contact include, but are not limited to: heart rate sensors, such as photoplethysmogram (PPG), heart rate variability (HRV) sensors, heart rate recovery (HRR) sensors, blood oxygenation (SpO2) sensors, blood pressure (BP) sensors, respiratory rate sensors, temperature sensors, inertial measurement unit (IMU) sensors, galvanic skin response (GSR) sensor, bio-impedance sensors, an electrocardiogram (ECG), glucose sensors, microphones, or own-voice sensors. One or more of these sensors can be used with the housing of the present subject matter. In various embodiments, it is beneficial to have an IMU sensor secured to the wearer's head to record actual head motion, to minimize noise. The housing of the present subject matter permits metallization in more areas of the housing without the loss of aesthetics, in various embodiments.

In addition, the housing of the present subject matter makes it possible to do transmissive optical measurement with a behind-the-ear portion of the hearing aid, such as a receiver-in-canal (RIC) hearing assistance device. In various embodiments, the behind-the-ear portion can be molded custom to the ear, or organically shaped to fit many or most ears. A RIC attachment is fit to the user or organically shaped to provide the correct pressure, and a RIC cable with the correct spring force, or magnets is used in various embodiments.

In addition to the stability of the shell, the present subject matter provides for other electronics to be embedded in the shell, because the shell of the present subject matter includes a large structure, such as a loop structure. In various embodiments, an antenna for wireless communication with the hearing device can be included in the housing. The antenna may include a Bluetooth antenna or other type of antenna, in various embodiments. Due to the size of the housing, a larger aperture antenna can be used than with a typical in-the-ear housing. In some embodiments, metals (such as steel, nitinol, tensile controlled material, etc.) can be included in the housing to provide a known contact pressure. The contact pressure can be optimized for the highest signal to noise ratio for the sensor (e.g. optical signal is maximized with a known pressure), in various embodiments. In various embodiments, nitinol, or other thermal memory materials, or electro active polymers, can be used to provide pressure for contact of the housing with the inner ear of the wearer. For example, a material can be used that expands with body temperature, to be easier to insert into the ear, but can still provide the correct pressure after insertion for the given sensor. Such materials can provide for easier insertion and withdrawal of the device for wearers with longer ear canals, in various embodiments. Some embodiments of the housing have a C-shape to provide for easier insertion into an ear of a wearer, while providing the same skin contact benefits.

Various embodiments of the present subject matter include a skim plate on a surface of the housing instead of a traditional thick faceplate. The skim plate is configured to cover and/or seal an opening in the housing after electronics are placed within an inner volume of the housing during manufacture and assembly of the device, in various embodiments. The skim plate provides for recovery of the electronics because the electronics are not completely encased in material from potting, as the skim plate allows for sealing the opening and electronics inside, but still provides for the ability to repair the device if portions of the electronics fail. For example, if the receiver fails the housing can be opened and the working parts can be removed and the non-working parts (in this example, the receiver) can be replaced.

The housing of the present subject matter provides a comfortable fit for a wearer with more continuous points of contact while being aesthetically pleasing to the wearer. In various embodiments, the housing is formed using an impression of a wearer's ear. In some embodiments, the housing is formed using a digital scan of the wearer's ear. The housing is formed by curing a resin with a light source, according to various embodiments. The housing may also be printed using a three-dimensional printing process, in some embodiments. The housing is contained within a conchal bowl or helix portion of the inner ear of the wearer, in various embodiments. In various embodiments, the housing includes a soft tip portion for easier insertion in the ear canal of the wearer. The soft tip portion may include silicone or other pliable material, in various embodiments. The soft tip portion provides for a better acoustic seal when inserted in the ear canal of the wearer.

Figure 1B:
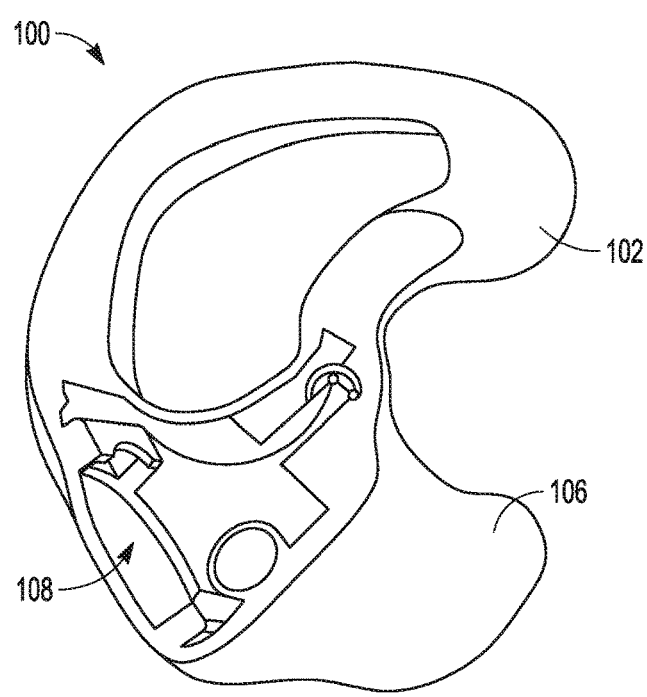

FIGS. 1A-1B illustrate a hearing assistance device housing 102 for improved biometric sensing, according to various embodiments of the present subject matter. In various embodiments, the housing 102 of a hearing assistance device 100 includes a surface 104 configured to conform to a continuous section of an inner portion of an ear of the wearer and to extend radially to one or more edges of a conchal bowl of the ear. The housing 102 further includes a biometric sensor 110 on the surface, and the housing 102 is configured to maintain contact of the biometric sensor 110 with the inner portion of the ear of the wearer during activity of the wearer, to enhance accuracy of biometric sensing, in various embodiments. The housing 102 may include a portion 106 for insertion into an ear canal of a wearer, in various embodiments. FIG. 1A illustrates the surface 104 for contact with the inner portion of the ear of the wearer. FIG. 1B illustrates a reverse view of the housing 102 showing the portion facing away from the inner portion of the ear when worn by the wearer. In various embodiments, the housing of the present subject matter includes a large loop structure. The housing is constructed of a material that is compliant to maintain contact with the inner portion of the ear of the wearer when the inner portion moves due to the activity, according to various embodiments.

In the depicted embodiment, the biometric sensor 110 is on or within a housing 102 of the hearing assistance device 100. The biometric sensor may protrude through an opening 108 in the housing 102, in an embodiment. The biometric sensor 110 may also be located on a surface of the housing 102, integrated with the housing 102 or external to the housing 102, in various embodiments. According to various embodiments, the biometric sensor includes one or more of a heart rate sensor, a temperature sensor, an inertial measurement unit (IMU), a galvanic skin response (GSR) sensor, an electrocardiogram (ECG), a glucose sensor, or a microphone. Other sensors may be used without departing from the scope of the present subject matter.

Figure 2:
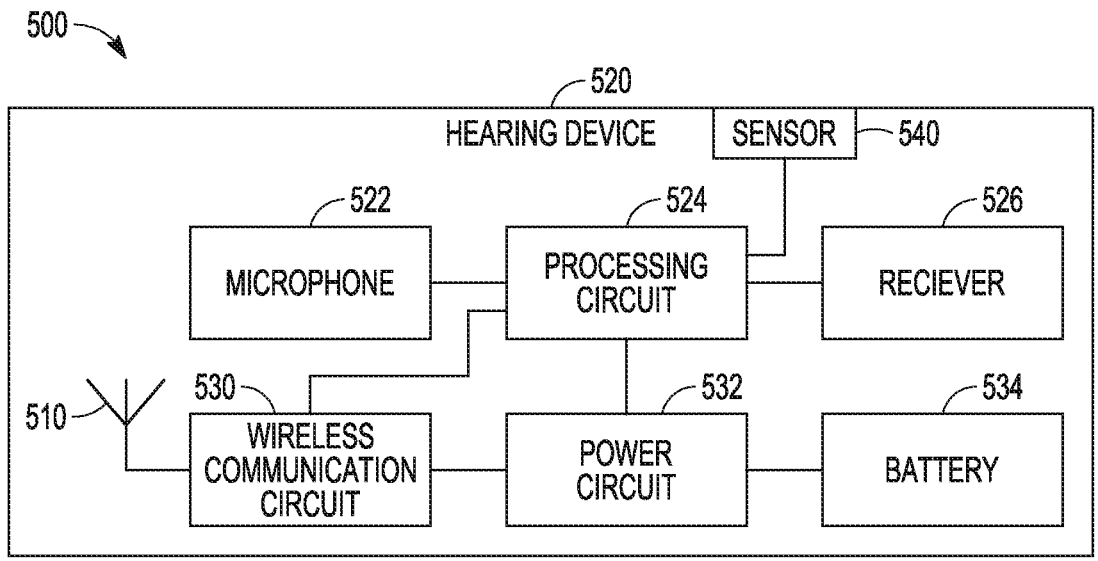
FIG. 2 illustrates a block diagram of a hearing assistance device including a housing for improved biometric sensing, according to various embodiments of the present subject matter.

FIG. 2 is a block diagram illustrating an exemplary embodiment of a hearing device 500 including a housing 520 for improved biometric sensing. Hearing device 500 includes a microphone 522, a wireless communication circuit 530, an antenna 510, a processing circuit 524, a receiver (speaker) 526, a battery 534, and a power circuit 532. Microphone 522 receives sounds from the environment of the hearing device wearer. Communication circuit 530 communicates with another device wirelessly using antenna 510, including receiving programming codes, streamed audio signals, and/or other audio signals and transmitting programming codes, audio signals, and/or other signals. Examples of the other device includes the other hearing aid of a pair of hearing aids for the same wearer, a hearing aid host device, an audio streaming device, a telephone, and other devices capable of communicating with hearing devices wirelessly.

Processing circuit 524 controls the operation of hearing device 500 using the programming codes and processes the sounds received by microphone 522 and/or the audio signals received by wireless communication circuit 530 to produce output sounds. Receiver 526 transmits output sounds to an ear canal of the hearing aid wearer. Battery 534 and power circuit 532 constitute the power source for the operation of processing circuit 524. In various embodiments, power circuit 532 can include a power management circuit. In various embodiments, battery 534 can include a rechargeable battery, and power circuit 532 can include a recharging circuit for recharging the rechargeable battery. The hearing device includes a sensor 540 on or in a surface of the housing 520, in various embodiments. The sensor 540 includes a biometric sensor in various embodiments (as shown in FIG. 1). One embodiments of the hearing device 500 of the present subject matter include only the sensor 540 on or in the housing 520. Other embodiments include one or more of additional electronic components on or within the housing 520, including one or more of those depicted in FIG. 2. Other electronic components may be included within the housing 520 without departing from the scope of the present subject matter. An additional housing (such as an above-the-ear housing) may be included as part of the hearing device, in various embodiments.

Figure 3:
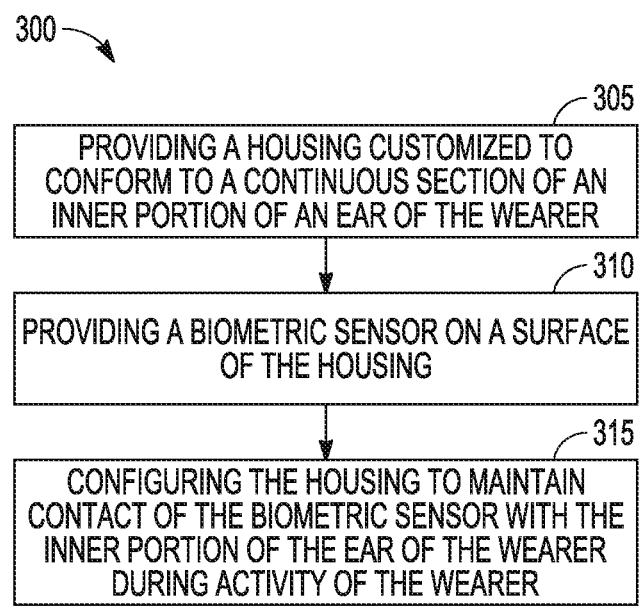
FIG. 3 illustrates a flow diagram of a method of forming a hearing assistance device, according to various embodiments of the present subject matter.

FIG. 3 illustrates a flow diagram of a method of forming a hearing assistance device for a wearer, according to various embodiments of the present subject matter. The method 300 includes providing a housing customized to conform to a continuous section of an inner portion of an ear of the wearer and to extend radially to one or more edges of a conchal bowl of the ear at step 305, the housing configured to be placed in the inner portion of the ear of the wearer. The method further includes providing a biometric sensor on a surface of the housing at step 310, according to various embodiments. The method also includes configuring the housing to maintain contact of the biometric sensor with the inner portion of the ear of the wearer during activity of the wearer at step 315, to enhance accuracy of biometric sensing, in various embodiments.

According to various embodiments, the method further includes providing a skim plate on the housing, the skim plate configured to cover and/or seal an opening in the housing. The housing is configured to provide continuous contact with the inner portion of the ear in at least three locations, in an embodiment. According to various embodiments, the hearing assistance device includes a hearing aid, including but not limited to a behind-the-ear (BTE) hearing aid, an on-the-ear (OTE) hearing aid, an in-the-ear (ITE) hearing aid, a completely-in-the-canal (CIC) hearing aid or a receiver-in-canal (RIC) hearing aid.

In some embodiments, an antenna for wireless communication with the hearing assistance device is included in the housing. According to various embodiments, the housing is a custom shell manufactured for the wearer using ear geometry of the wearer. The housing is manufactured using an impression of an ear canal of the wearer, in some embodiments. The housing includes a plastic material, in various embodiments. According to various embodiments, the housing includes a metal with a spring characteristic to provide a constant force to ensure continuous contact with the inner portion of the ear of the wearer. The housing includes one or more of a thermal memory material or an electroactive polymer, in some embodiments.

Figure 4A:
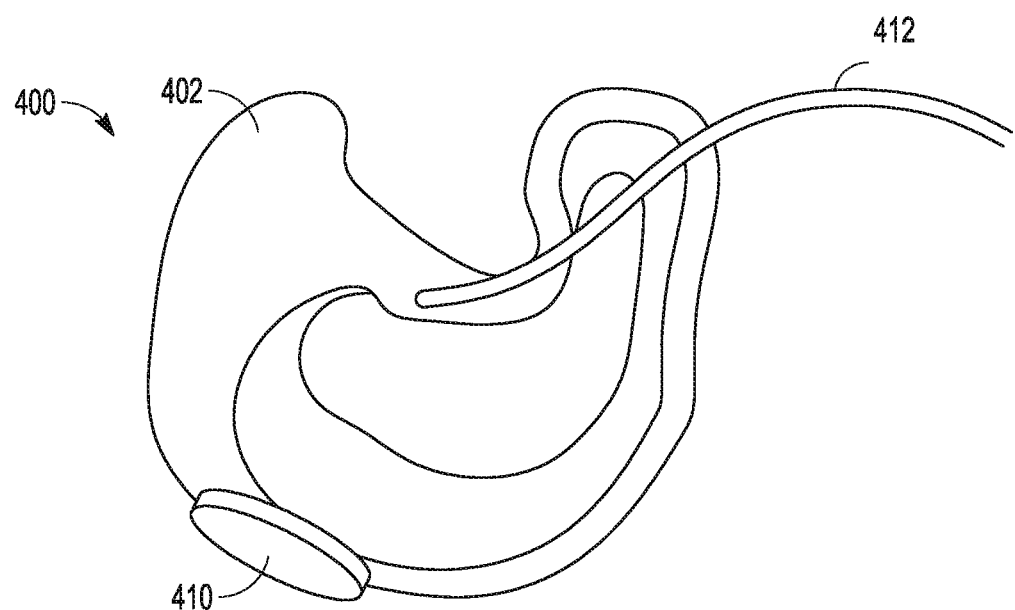
FIGS. 4A-4B illustrate a receiver-in-canal (RIC) hearing assistance device housing for improved biometric sensing, according to various embodiments of the present subject matter.
Figure 4B:
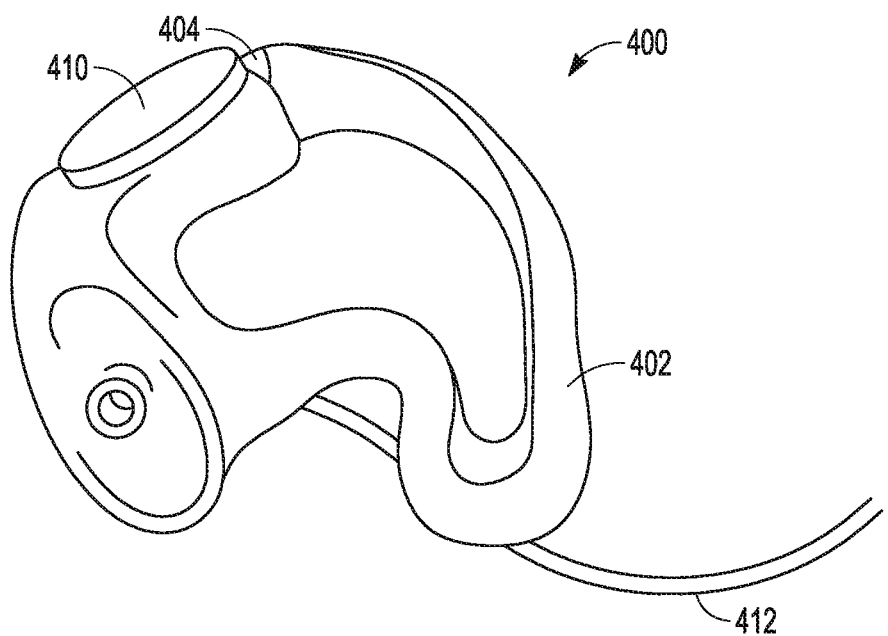

FIGS. 4A-4B illustrate a receiver-in-canal (RIC) hearing assistance device housing 402 for improved biometric sensing, according to various embodiments of the present subject matter. In various embodiments, a hearing assistance device 400 for a wearer includes a housing 402 customized to conform to a continuous section of an inner portion of an ear of the wearer and to extend radially to one or more edges of a conchal bowl of the ear. The housing 402 is configured to be placed in the inner portion of the ear of the wearer, and a biometric sensor 410 is included on a surface of the housing. According to various embodiments, the housing 402 is configured to maintain contact of the biometric sensor 410 with the inner portion of the ear of the wearer during activity of the wearer, to enhance accuracy of biometric sensing. Some embodiments include a gap or void in the housing, such that the housing forms a loop structure.

The depicted hearing assistance device is a RIC device having a cable 412 configured to connect to an above-the-ear or behind-the-ear housing incorporating additional hearing assistance electronics. By using the housing 402 with a RIC type hearing aid, sensors can readily be added in the ear because the hearing aid electronics are located above or behind the ear. FIG. 4B illustrates the surface 404 for contact with the inner portion of the ear of the wearer. FIG. 4A illustrates a reverse view of the housing 402 showing the portion facing away from the inner portion of the ear when worn by the wearer.

Figure 5A:
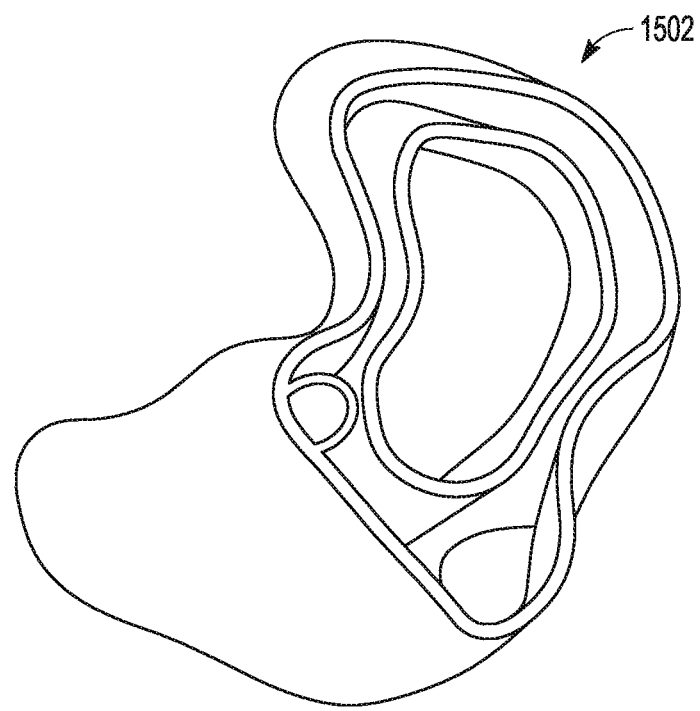
FIGS. 5A-5D illustrate various views of a hearing assistance device housing for improved biometric sensing, according to various embodiments of the present subject matter.
Figure 5B:
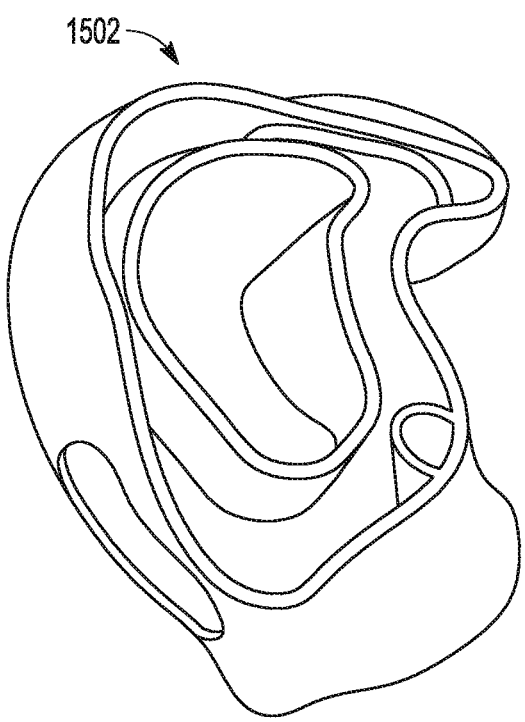
Figure 5C:
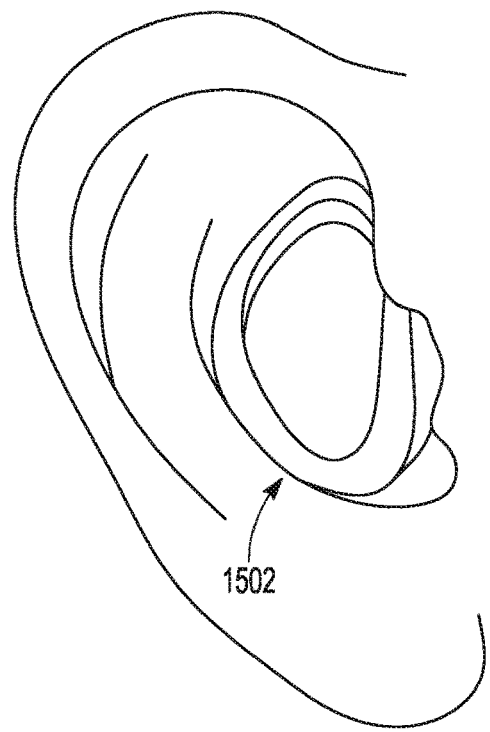
Figure 5D:
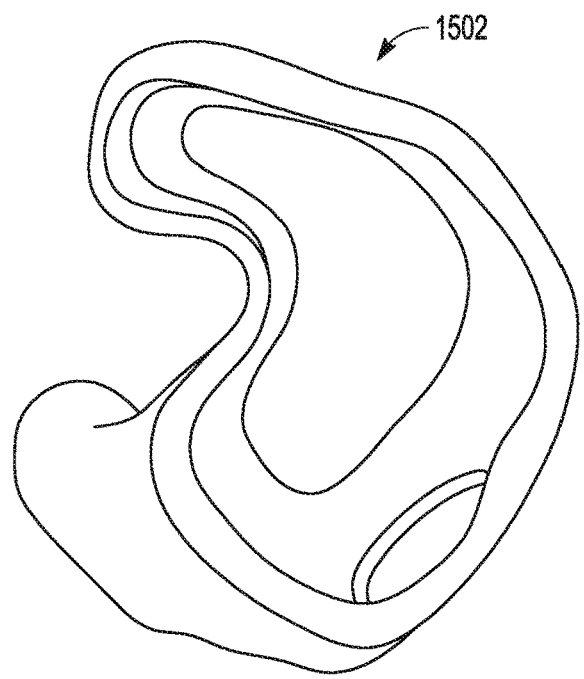

FIGS. 5A-5D illustrate various views of a hearing assistance device housing for improved biometric sensing, according to various embodiments of the present subject matter. FIGS. 5A, 5B and 5D illustrate various sizes of housing 1502 for improved biometric sensing, in various embodiments. FIG. 5C illustrates an embodiment of the housing 1502 in an ear of a wearer.

Figure 6A:
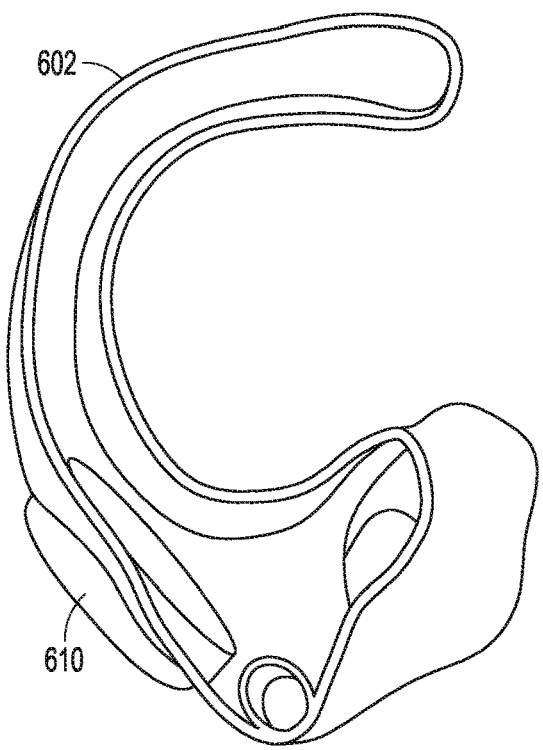
FIGS. 6A-6B illustrate a C-shaped hearing assistance device housing for improved biometric sensing, according to various embodiments of the present subject matter.
Figure 6B:
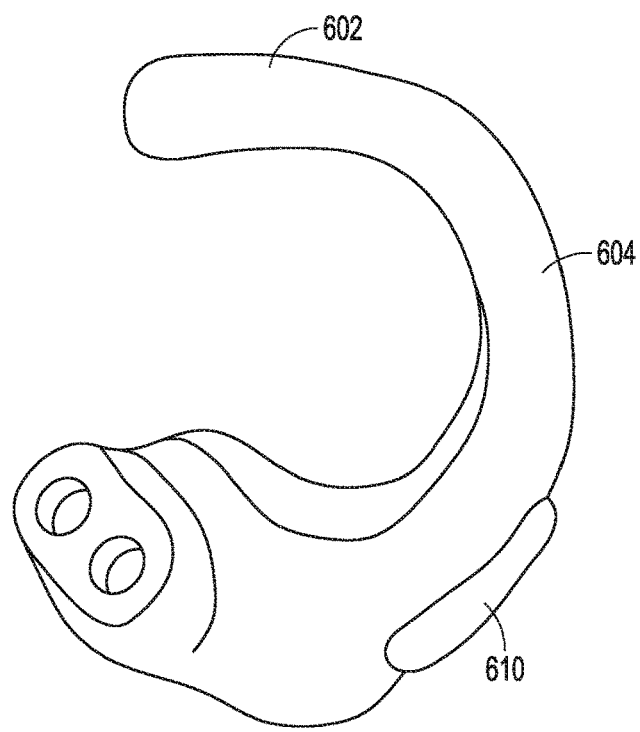

FIGS. 6A-6B illustrate a C-shaped hearing assistance device housing 602 for improved biometric sensing, according to various embodiments of the present subject matter. The housing 602 is configured to be placed in the inner portion of the ear of the wearer, and a biometric sensor 610 is included on a surface of the housing. FIG. 6B illustrates the surface 604 for contact with the inner portion of the ear of the wearer. FIG. 6A illustrates a reverse view of the housing 602 showing the portion facing away from the inner portion of the ear when worn by the wearer. Other shapes of the housing 602 can be used without departing from the scope of the present subject matter.

In the depicted embodiment, the biometric sensor 610 is on or within a housing 602. The biometric sensor 610 may also be located on a surface of the housing 602, integrated with the housing 602 or external to the housing 602, in various embodiments.

Various embodiments of the present subject matter support wireless communications with a hearing assistance device. In various embodiments the wireless communications may include standard or nonstandard communications. Some examples of standard wireless communications include link protocols including, but not limited to, Bluetooth™, Bluetooth™ Low Energy (BLE), IEEE 802.11 (wireless LANs), 802.15 (WPANs), 802.16 (WiMAX), cellular protocols including, but not limited to CDMA and GSM, ZigBee, and ultra-wideband (UWB) technologies. Such protocols support radio frequency communications and some support infrared communications. Although the present system is demonstrated as a radio system, it is possible that other forms of wireless communications may be used such as ultrasonic, optical, infrared, and others. It is understood that the standards which may be used include past and present standards. It is also contemplated that future versions of these standards and new future standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, SPI, PCM, ATM, Fibre-channel, Firewire or 1394, InfiniBand, or a native streaming interface. In various embodiments, such connections include all past and present link protocols. It is also contemplated that future versions of these protocols and new future standards may be employed without departing from the scope of the present subject matter.

Hearing assistance devices typically include at least one enclosure or housing, a microphone, hearing assistance device electronics including processing electronics, and a speaker or "receiver." Hearing assistance devices may include a power source, such as a battery. In various embodiments, the battery is rechargeable. In various embodiments multiple energy sources are employed. It is understood that in various embodiments the microphone is optional. It is understood that in various embodiments the receiver is optional. It is understood that variations in communications protocols, antenna configurations, and combinations of components may be employed without departing from the scope of the present subject matter. Antenna configurations may vary and may be included within an enclosure for the electronics or be external to an enclosure for the electronics. Thus, the examples set forth herein are intended to be demonstrative and not a limiting or exhaustive depiction of variations.

It is understood that digital hearing assistance devices include a processor. In digital hearing assistance devices with a processor, programmable gains may be employed to adjust the hearing assistance device output to a wearer's particular hearing impairment. The processor may be a digital signal processor (DSP), microprocessor, microcontroller, other digital logic, or combinations thereof. The processing may be done by a single processor, or may be distributed over different devices. The processing of signals referenced in this application may be performed using the processor or over different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments of the present subject matter the processor is adapted to perform instructions stored in one or more memories, which may or may not be explicitly shown. Various types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments of the present subject matter, different realizations of the block diagrams, circuits, and processes set forth herein may be created by one of skill in the art without departing from the scope of the present subject matter.

It is further understood that different hearing assistance devices may embody the present subject matter without departing from the scope of the present disclosure. The devices depicted in the figures are intended to demonstrate the subject matter, but not necessarily in a limited, exhaustive, or exclusive sense. It is also understood that the present subject matter may be used with a device designed for use in the right ear or the left ear or both ears of the wearer.

The present subject matter is demonstrated for hearing assistance devices, including hearing assistance devices, including but not limited to, behind-the-ear (BTE), in-the-ear (ITE), in-the-canal (ITC), receiver-in-canal (RIC), invisible-in-canal (IIC) or completely-in-the-canal (CIC) type hearing assistance devices. It is understood that behind-the-ear type hearing assistance devices may include devices that reside substantially behind the ear or over the ear. Such devices may include hearing assistance devices with receivers associated with the electronics portion of the behind-the-ear device, or hearing assistance devices of the type having receivers in the ear canal of the user, including but not limited to receiver-in-canal (RIC) or receiver-in-the-ear (RITE) designs. The present subject matter may also be used in hearing assistance devices generally, such as cochlear implant type hearing devices. The present subject matter may also be used in deep insertion devices having a transducer, such as a receiver or microphone. The present subject matter may be used in devices whether such devices are standard or custom fit and whether they provide an open or an occlusive design. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A hearing assistance device for a wearer, comprising:
a housing customized to conform to a continuous section of an inner portion of an ear of the wearer and to extend radially to one or more edges of a conchal bowl of the ear, the housing configured to be placed in the inner portion of the ear of the wearer; and
a biometric sensor on a surface of the housing,
wherein the housing is configured to maintain contact of the biometric sensor with the inner portion of the ear of the wearer during activity of the wearer, to enhance accuracy of biometric sensing.

2. The device of claim 1, further comprising:
an antenna for wireless communication with the hearing assistance device, wherein the antenna is included in the housing.

3. The device of claim 1, wherein the biometric sensor includes one or more of a heart rate sensor, a temperature sensor, an inertial measurement unit (IMU), a galvanic skin response (GSR) sensor, an electrocardiogram (ECG), a glucose sensor, or a microphone.

4. The device of claim 1, wherein the housing is a custom shell manufactured for the wearer using ear geometry of the wearer.

5. The device of claim 4, wherein the housing is manufactured using an impression of an ear canal of the wearer.

6. The device of claim 1, wherein the housing includes a plastic material.

7. The device of claim 1, wherein the housing includes a metal with a spring characteristic to provide a constant force to ensure continuous contact with the inner portion of the ear of the wearer.

8. The device of claim 1, wherein the housing includes one or more of a thermal memory material or an electroactive polymer.

9. The device of claim 1, wherein the hearing assistance device includes a hearing aid.

10. The device of claim 9, wherein the hearing aid includes a behind-the-ear (BTE) hearing aid.

11. The device of claim 9, wherein the hearing aid includes an on-the-ear (OTE) hearing aid.

12. The device of claim 9, wherein the hearing aid includes an in-the-ear (ITE) hearing aid.

13. The device of claim 9, wherein the hearing aid includes a completely-in-the-canal (CIC) hearing aid.

14. The device of claim 9, wherein the hearing aid includes a receiver-in-canal (RIC) hearing aid.

15. A housing for a hearing assistance device, the housing comprising:
a surface configured to conform to a continuous section of an inner portion of an ear of the wearer and to extend radially to one or more edges of a conchal bowl of the ear;
a biometric sensor on the surface,
wherein the housing is configured to maintain contact of the biometric sensor with the inner portion of the ear of the wearer during activity of the wearer, to enhance accuracy of biometric sensing.

16. The housing of claim 15, wherein the biometric sensor includes one or more of a heart rate sensor, a temperature sensor, an inertial measurement unit (IMU), a galvanic skin response (GSR) sensor, an electrocardiogram (ECG), a glucose sensor, or a microphone.

17. The housing of claim 16, wherein the housing includes a C-shaped housing.

18. A method of forming a hearing assistance device for a wearer, comprising:
providing a housing customized to conform to a continuous section of an inner portion of an ear of the wearer and to extend radially to one or more edges of a conchal bowl of the ear, the housing configured to be placed in the inner portion of the ear of the wearer; and
providing a biometric sensor on a surface of the housing,
configuring the housing to maintain contact of the biometric sensor with the inner portion of the ear of the wearer during activity of the wearer, to enhance accuracy of biometric sensing.

19. The method of claim 18, further comprising:
providing a skim plate on the housing, the skim plate configured to cover an opening in the housing.

20. The method of claim 18, wherein providing the housing includes providing a housing configured to provide continuous contact with the inner portion of the ear in at least three locations.

* * * * *